United States Patent
Stefinovic et al.

(10) Patent No.: US 10,053,427 B2
(45) Date of Patent: Aug. 21, 2018

(54) CRYSTALLINE FORMS OF CABOZANTINIB PHOSPHATE AND CABOZANTINIB HYDROCHLORIDE

(71) Applicant: Sandoz AG, Basel (CH)

(72) Inventors: Marijan Stefinovic, Kundl (AT); Erwin Paul Schreiner, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 15/560,527

(22) PCT Filed: Mar. 22, 2016

(86) PCT No.: PCT/EP2016/056267
§ 371 (c)(1),
(2) Date: Sep. 22, 2017

(87) PCT Pub. No.: WO2016/150966
PCT Pub. Date: Sep. 29, 2016

(65) Prior Publication Data
US 2018/0111903 A1 Apr. 26, 2018

(30) Foreign Application Priority Data

Mar. 25, 2015 (EP) .................................... 15160869

(51) Int. Cl.
C07D 215/233 (2006.01)
A61K 31/47 (2006.01)
A61P 35/00 (2006.01)

(52) U.S. Cl.
CPC .......... C07D 215/233 (2013.01); A61P 35/00 (2018.01); *C07B 2200/13* (2013.01)

(58) Field of Classification Search
None
See application file for complete search history.

(56) References Cited

FOREIGN PATENT DOCUMENTS

| CN | 104109124 | 10/2014 |
|---|---|---|
| WO | 2005030410 A2 | 4/2005 |
| WO | 2010083414 A1 | 7/2010 |

OTHER PUBLICATIONS

International Search Report and Written Opinion for PCT/EP2016/056267, dated Sep. 29, 2016.

*Primary Examiner* — Emily A Bernhardt
(74) *Attorney, Agent, or Firm* — Luedeka Neely Group, P.C.

(57) ABSTRACT

The present invention relates to crystalline forms of cabozantinib phosphoric acid salt and cabozantinib hydrochloric acid salt and to a method for their preparation. Furthermore, the invention relates to pharmaceutical compositions comprising said crystalline forms and their use as anti-cancer medicaments. Cabozantinib, i.e. N-{4-[(6,7-dimethoxy-4-quinolinyl)oxy]phenyl}-N'-(4-fluorophenyl)-1,1-cyclopropanedicarboxamide is represented by the chemical structure: Formula.

13 Claims, 7 Drawing Sheets

Phosphate

Hydrochloride

CRYSTALLINE FORMS OF CABOZANTINIB PHOSPHATE AND CABOZANTINIB HYDROCHLORIDE

This application is a Section 371 national phase entry of PCT application PCT/EP2016/056267, filed Mar. 22, 2016. This application also claims the benefit of the earlier filing date of European patent application 15160869.2, filed Mar. 25, 2015.

FIELD OF THE INVENTION

The present invention relates to a crystalline form of cabozantinib phosphate and a crystalline form of cabozantinib hydrochloride and to a method for their preparation. Furthermore, the invention relates to pharmaceutical compositions comprising said crystalline forms and their use as anti-cancer medicaments.

BACKGROUND OF THE INVENTION

N-{4-[(6,7-dimethoxy-4-quinolinyl)oxy]phenyl}-N'-(4-fluorophenyl)-1,1-cyclopropanedicarboxamide (international non-proprietary name (INN): cabozantinib) represented by chemical structure

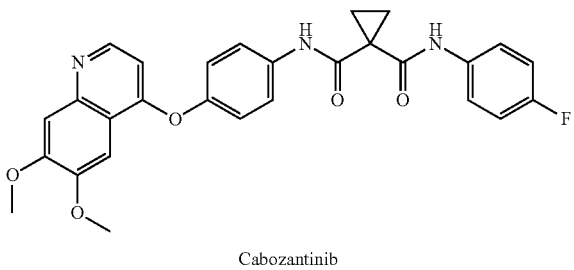 [SMILES: COc1cc2nccc(Oc3ccc(NC(=O)C4(C(=O)Nc5ccc(F)cc5)CC4)cc3)c2cc1OC]

Cabozantinib is a RET, MET, KIT and VEGFR2 receptor tyrosine kinase inhibitor. It is currently marketed for the treatment of thyroid cancer under the brand name Cometriq. Cometriq capsules contain cabozantinib as its (L)-malate salt. Cabozantinib is classified as a BCS class II compound having a low solubility and high permeability. The malate salt shows an enhanced solubility when compared with cabozantinib free base.

The above mentioned compound will be referred to in the present application by its international non-proprietary name, i.e. cabozantinib. A salt of cabozantinib will be referred to as cabozantinib salt, e.g. cabozantinib phosphate or cabozantinib phosphate salt.

International patent application WO2005/030140A2 discloses cabozantinib. Further, this application discloses processes for the preparation of cabozantinib, pharmaceutical preparations of cabozantinib and therapeutic applications thereof.

Patent application CN 104109124 discloses cabozantinib 0.5 malate crystal, pharmaceutical compositions and therapeutic applications thereof for the treatment of tumor associated diseases. The crystal is characterized by a power X-ray diffraction pattern comprising the diffraction peaks at 2theta angles: 5.48, 10.88, 15.24, 21.97, 24.56 when measured using Cu-Ka radiation.

International patent application WO2010/083414 A1 discloses the (L)-, (D)- and (D,L)-malate salts as compounds (I), (II) and (III). WO2010/083414 further discloses the polymorphic Forms N-1 and N-2 of compounds (I) (II) and (III). The (L)-malate salt is reported to be non-hygroscopic and having chemical stability.

Example 1 of WO2010/083414 provides a concrete process for the preparation of cabozantinib free base. Example 2 provides a concrete process for the preparation of cabozantinib (L)-malate crystalline Form N-1 comprising a final crystallization step from acetonitrile as the solvent. XRPD spectrum of (L)-malate crystalline Form N-1 is also disclosed. Example 4 provides a concrete process for the preparation of cabozantinib (L)-malate crystalline Form N-2 comprising a final crystallization step from a binary system of solvents wherein the solvents are tetrahydrofuran and methyl isobutyl ketone. Seeds are required for crystallization of Form N-2. XRPD spectrum of (L)-malate crystalline Form N-2 is also disclosed. Form N-2 has been selected for commercial development.

Hence, the cabozantinib (L)-malate salt exists in two polymorphic forms that need to be controlled in the formulation of the drug.

Further, WO2010/083414 discloses a cabozantinib phosphate salt which is poorly soluble and hygroscopic. The salt is reported to exhibit a 8 weight-% gain due to water absorption.

Further, WO2010/083414 discloses a cabozantinib hydrochloride salt. Possible hydrate formation and a phase change upon humidity (75%) and high temperature (40° C.) are reported.

In view of the above mentioned drawbacks, there is the need to provide forms of cabozantinib with physicochemical properties which render them suitable for pharmaceutical formulation; in particular solid forms with a balanced profile of appropriate physicochemical properties such as suitable solubility, chemical stability, favorable morphology, improved filterability, appropriate hygroscopicity. There is, as well, the need for pharmaceutical compositions comprising the same.

SUMMARY OF THE INVENTION

The present invention relates to crystalline non-hygroscopic and anhydrous salt forms of cabozantinib. In particular, the present invention relates to a crystalline form of a cabozantinib phosphate and to a crystalline form of a cabozantinib hydrochloride. These crystalline forms of the invention are anhydrous and non-hygroscopic. They show chemical as well as physical stability and/or appropriate solubility. Furthermore, the crystalline forms of the present invention comprise crystals with especially suitable morphology for the production of pharmaceutical drug products and which can be easily filtered.

Definitions

In the context of the present invention the following abbreviations have the indicated meaning, unless explicitly stated otherwise:

XRPD powder X-ray diffraction/diffractogram
TG/DTA thermogravimetric/differential thermal analysis
DVS dynamic vapor sorption
PLM polarized light microscopy
NMR nuclear magnetic resonance
HPLC-UV High performance liquid chromatography-ultraviolet detection
KF Karl Fischer Coulometric Titration
RT room temperature
RH relative humidity m mass
Δm mass change
hr heating rate As used herein the term "room temperature" relates to temperatures between 15 and 25° C. [see e.g. European Pharmacopoeia 8.3, 1.2 (2015)].

As used herein, the term "mother liquor" refers to the solution remaining after crystallization of a solid.

The term "non-hygroscopic" as used herein refers to compounds showing a weight change of less than 1.2 weight-% based on the weight of the compound in the range of from 20 to 70% relative humidity at (25.0±0.1) ° C.

The term "essentially the same" with reference to XRPD means that variability in peak positions and relative intensities of the peaks are to be taken into account. For example, a typical precision of the 2-Theta values is in the range of ±0.2° 2-Theta. Thus, a diffraction peak that usually appears at 14.9° 2-Theta for example can appear between 14.7° and 15.1° 2-Theta on most X-ray diffractometers under standard conditions. Furthermore, one skilled in the art will appreciate that relative peak intensities will show inter-apparatus variability as well as variability due to degree of crystallinity, preferred orientation, sample preparation and other factors known to those skilled in the art and should be taken as qualitative measure only. Typically, XRPD measurements are done at a temperature of 20° C., preferably also at a relative humidity of 40%.

The term "Form N-1" as used herein refers to the crystalline form of cabozantinib (L)-malate disclosed in WO2010/083414 A1 which is characterized by having a XRPD comprising reflections at 2-Theta angles of (12.8±0.2)°, (13.5±0.2)°, (16.9±0.2)°, (19.4±0.2)°, (21.5±0.2)°, (22.8-0.2)°, (25.1±0.2)°, (26.6±0.2)°, when measured at 20° C. with Cu-Kalpha radiation having a wavelength of 0.15419 nm. Alternatively, Form N-1 as used herein refers to the form of cabozantinib (L)-malate disclosed in paragraph [0056] pages 10 to 11 of WO2010/083414 and having a XRPD as disclosed on FIG. 1 as therein disclosed.

The term "Form N-2" as used herein refers to the crystalline form of cabozantinib (L)-malate disclosed in WO 2010/083414 A1 which is characterized by having a XRPD comprising four or more reflections at 2-Theta angles selected from (6.4±0.2)°, (9.1±0.2)°, (12.0±0.2)°, (12.8±0.2)°, (13.7±0.2)°, (17.1±0.2°), (20.9±0.2)°, (21.9±0.2)°, (22.6±0.2)°, (23.7±0.2)°, when measured at 20° C. with Cu-Kalpha radiation having a wavelength of 0.15419 nm. Alternatively, Form N-2 as used herein refers to the form of cabozantinib (L)-malate disclosed in paragraph [0058] page 11 of WO2010/083414 and having a XRPD as disclosed on FIG. 8 as therein disclosed.

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the mentioned diffraction angles. Consequently, it is to be understood that the crystal forms of the present invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

The term "cabozantinib phosphate" or "cabozantinib phosphate salt" as used herein refers to a salt between cabozantinib and phosphoric acid. Phosphoric acid is a triprotic acid and can form dihydrogenphosphate, i.e. a monoanion where one of the three acidic hydroxyl functions is deprotonated, hydrogenphosphate, i.e. a dianion where two of the three acidic hydroxyl functions are deprotonated, and phosphates, i.e. a trianion where all of the three acidic hydroxyl functions are deprotonated. Salts with all forms of deprotonated phosphoric acid are included in the general term "phosphate salt" as used herein, and salts with dihydrogenphosphate and/or hydrogenphosphate are preferred. A most preferred meaning for "cabozantinib phosphate" is "cabozantinib dihydrogenphosphate".

As used herein, the term "substantially pure" with reference to a particular polymorphic form of a salt means that the polymorphic form includes less than 10%, preferably less than 5%, more preferably less than 3%, most preferably less than 1% by weight of any other physical form of the salt.

DETAILED DESCRIPTION OF THE INVENTION

Figure 1:
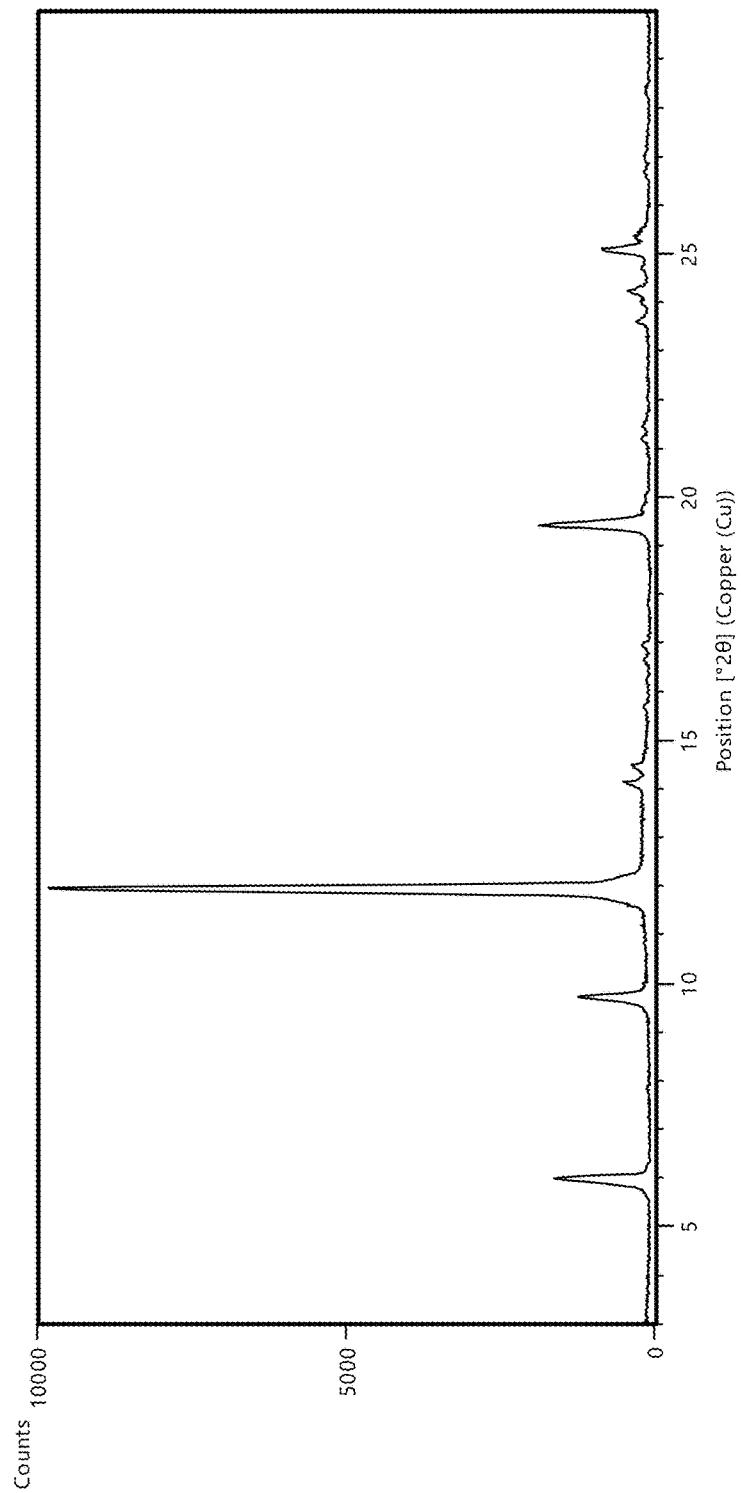
FIG. 1: Representative XRPD of the crystalline Form A of cabozantinib phosphate according to the present invention.

The invention is described below in further details, without being limited thereto.

Crystalline Cabozantinib Phosphate and Cabozantinib Hydrochloride

The present invention relates to crystalline salts of cabozantinib with phosphoric acid and hydrochloric acid, respectively. In particular, the present invention relates to crystalline cabozantinib phosphate and to crystalline cabozantinib hydrochloride.

The crystalline forms of the invention may be characterized by analytical methods well known in the field of the pharmaceutical industry for characterizing solids. Such methods comprise but are not limited to XRPD, TG/DTA, KF, $^1$H NMR and DVS.

In one aspect, the present invention relates to a crystalline form of cabozantinib phosphate salt, hereinafter also designated as "Form A".

In another aspect, the present invention relates to a crystalline form of cabozantinib hydrochloride salt, hereinafter also designated as "Form A-1".

Cabozantinib phosphate Form A and cabozantinib hydrochloride Form A-1 may be characterized by one of the aforementioned analytical methods or by combining two or more of them. In particular, cabozantinib phosphate Form A and cabozantinib hydrochloride Form A-1 may be characterized by any one of the following aspects or by combining two or more of the following aspects.

Cabozantinib phosphate Form A and cabozantinib hydrochloride Form A-1 of the present invention can for example be characterized by their XRPD. Table 1 provides reflections for cabozantinib phosphate Form A and for cabozantinib hydrochloride Form A-1. One or more of these reflections, preferably one or more, such as all, of the reflections marked in bold, may be used to characterize the respective crystalline form.

TABLE 1

Cabozantinib phosphate Form A and Cabozantinib hydrochloride Form A-1 reflections

| Cabozantinib phosphate Form A Reflections [±0.2 °2Th.] | Cabozantinib hydrochloride Form A-1 Reflections [±0.2 °2Th.] |
|---|---|
| 6.0 | 6.9 |
| 9.7 | 7.1 |
| 12.0 | 7.9 |
| 14.1 | 8.9 |
| 14.5 | 9.4 |
| 15.7 | 11.2 |
| 16.2 | 11.6 |
| 16.6 | 11.9 |
| 17.7 | 12.7 |
| 17.8 | 13.4 |
| 19.4 | 14.2 |
| 19.8 | 14.7 |
| 20.0 | 15.7 |
| 21.2 | 16.3 |
| 21.5 | 17.2 |
| 23.6 | 18.0 |
| 24.0 | 18.6 |
| 24.2 | 19.3 |
| 24.7 | 20.0 |
| 25.1 | 20.7 |
| 25.4 | 21.3 |
| 26.7 | 21.9 |
| 27.0 | 22.3 |
| 28.4 | 22.8 |
| | 23.2 |
| | 23.6 |
| | 24.2 |
| | 25.4 |
| | 26.4 |
| | 27.5 |
| | 29.0 |
| | 29.9 |

Cabozantinib Phosphate Form A

WO2010/083414 discloses a cabozantinib phosphate salt which is poorly soluble and hygroscopic. The cabozantinib phosphate salt from WO2010/083414 is reported to exhibit a 8 weight-% gain due to water absorption. It was thus surprising that an anhydrous and non-hygroscopic form of cabozantinib phosphate could be prepared.

Preferably, cabozantinib phosphate Form A is characterized by having a XRPD comprising reflections at 2-Theta angles of (6.0±0.2)°, (9.7±0.2)°, (12.0±0.2)°, when measured at 20° C. with Cu-Kalpha radiation having a wavelength of 0.15419 nm.

More preferably, cabozantinib phosphate Form A is characterized by having a XRPD comprising reflections at 2-Theta angles of (6.0±0.2)°, (9.7±0.2)°, (12.0±0.2)°, (19.4±0.2)°, when measured at 20° C. with Cu-Kalpha radiation having a wavelength of 0.15419 nm.

Particularly, cabozantinib phosphate Form A is characterized by having a XRPD comprising reflections at one or more 2-Theta angles selected from the group of (6.0±0.2)°, (9.7±0.2)°, (12.0±0.2)°, (19.4±0.2)°, (25.1±0.2)°, when measured at 20° C. with Cu-Kalpha radiation having a wavelength of 0.15419 nm.

Further, cabozantinib phosphate Form A is characterized by having a XRPD comprising additional one or more reflections, such as two additional reflections, three additional reflections, four additional reflections or even five additional reflections, at 2-Theta angles selected from the group of (14.1±0.2)°, (14.5±0.2)°, (23.6±0.2)°, (24.2±0.2)°, (25.1±0.2)°, when measured at 20° C. with Cu-Kalpha radiation having a wavelength of 0.15419 nm, in particular as disclosed in reference example A) herein.

Still further cabozantinib phosphate Form A is characterized by having a XRPD characterized further comprising five or more, such as six, seven, eight or even nine, reflections at 2-Theta angles selected from the group of (15.7±0.2)°, (16.2±0.2)°, (16.6±0.2)°, (17.7±0.2)°, (20.0±0.2)°, (21.5±0.2)°, (24.7±0.2)°, (26.7±0.2)°, (27.0±0.2)° and (28.4±0.2)°, when measured at 20° C. with Cu-Kalpha radiation having a wavelength of 0.15419 nm, in particular as disclosed in reference example A) herein.

Alternatively, cabozantinib phosphate Form A can be characterized by showing a XRPD comprising peaks at all of the positions shown in bold in Table 1-first column, when measured at 20° C. with Cu-Kalpha radiation having a wavelength of 0.15419 nm. Alternatively, cabozantinib phosphate Form A can be characterized by showing a XRPD comprising peaks at all of the positions shown in Table 1-first column, when measured at 20° C. with Cu-Kalpha radiation having a wavelength of 0.15419 nm. Alternatively, cabozantinib phosphate Form A can be characterized by showing a XRPD which is essentially the same as displayed in FIG. 1 of the present invention, when measured at 20° C. with Cu-Kalpha radiation having a wavelength of 0.15419 nm.

Alternatively or additionally, cabozantinib phosphate Form A can be characterized by having a TG/DTA curve showing a weight loss of at most 1 weight-%, such as at most 0.5 weight-%, preferably in the range of from 0.2 to 0.4 weight-% based on the weight of cabozantinib phosphate Form A, when measured at a temperature in the range of from 25 to 210° C. and a heating rate of about 10° C./min, in particular when measured according to reference example B) herein below.

Figure 3:
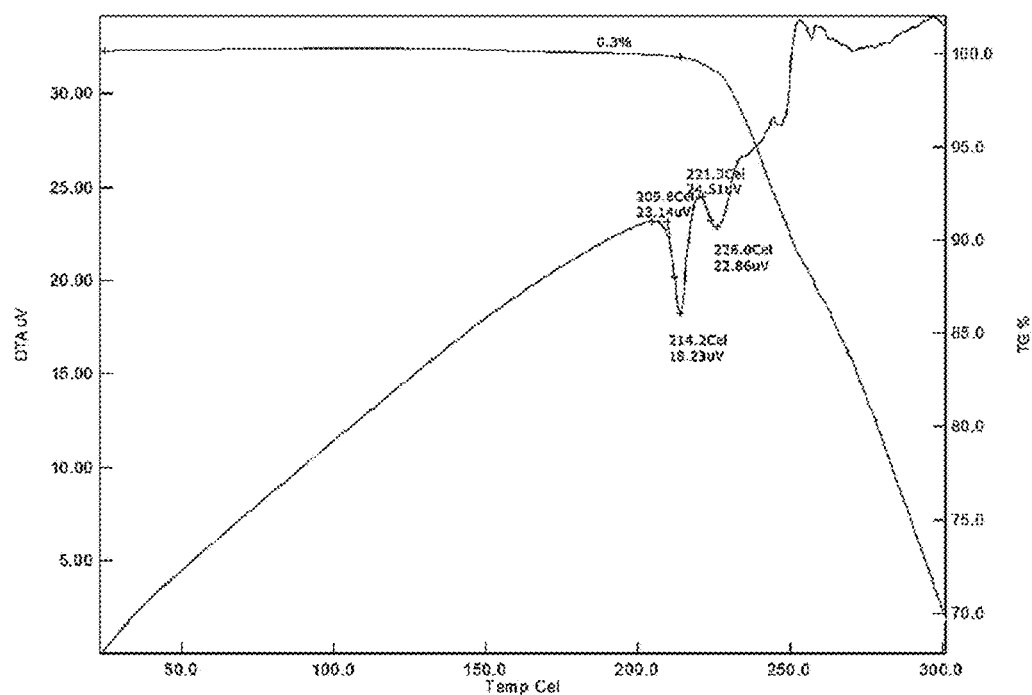
FIG. 3: Representative TG/DTA curve of the crystalline Form A of cabozantinib phosphate according to the present invention.

Alternatively or additionally, cabozantinib phosphate Form A can be characterized by having a TG/DTA curve as disclosed in FIG. 3, in particular when measured according to reference example B), herein.

Alternatively or additionally, cabozantinib phosphate Form A can be characterized by showing a water content of at most 1.0 weight-%, such as at most 0.7 weight-% based on the weight of the crystalline Form A, when determined by KF in particular as disclosed in reference example F) herein. Preferably, the water content is in the range of from 0.4 to 0.6 weight-% based on the weight of the crystalline Form A, when determined by KF in particular as disclosed in reference example F) herein.

Alternatively or additionally, cabozantinib phosphate Form A can be characterized as being an anhydrous crystalline form and most preferably a non-solvated and anhydrous crystalline form.

Alternatively or additionally, cabozantinib phosphate Form A can be characterized as being non-hygroscopic.

Alternatively or additionally, cabozantinib phosphate Form A can be characterized by comprising particles having rod-like shape.

Preferably, cabozantinib phosphate Form A is provided in substantially pure form.

Preferably, cabozantinib phosphate Form A has substantially pure phase homogeneity as indicated by less than 10%, preferably less than 5%, and more preferably less than 2% of the total peak area in the experimentally measured XRPD pattern arising from the extra peaks that are absent from the simulated XRPD pattern. Most preferred is a crystalline form of cabozantinib phosphate Form A having substantially pure phase homogeneity with less than 1% of the total peak area in the experimentally measured XRPD pattern arising from the extra peaks that are absent from the simulated XRPD pattern. In the present context the term "extra peaks" refers to XRPD peaks that do not belong or are not assigned to Form A.

In one embodiment, a composition is provided consisting essentially of the cabozantinib phosphate form A. The composition of this embodiment may comprise at least 90 weight % of cabozantinib phosphate Form A, based on the weight of cabozantinib phosphate in the composition. The composition comprises preferably at least 95 weight-% of cabozantinib phosphate Form A, more preferably at least 97 weight-% of cabozantinib phosphate Form A, even more preferably at least 99 weight-% of cabozantinib phosphate Form A, based on the weight of cabozantinib phosphate in the composition.

The presence of more than one polymorph in a sample may be determined by techniques such as X-ray powder diffraction (XRPD) or solid state nuclear magnetic resonance spectroscopy. For example, the presence of extra peaks in the comparison of an experimentally measured XRPD pattern with a simulated XRPD pattern may indicate more than one polymorph in the sample. The simulated XRPD may be calculated from single crystal x-ray data as disclosed in Smith, D. K., "A FORTRAN Program for Calculating X-Ray Powder Diffraction Patterns," Lawrence Radiation Laboratory, Livermore, Calif., UCRL-7196 (April 1963) or TOPAS program (Total Pattern Analysis Solution, available through Bruker AXS Inc.) herein incorporated by reference.

Preferably, in cabozantinib phosphate Form A, the molar ratio of the cabozantinib relative to the phosphorous is in the range of from 1:0.5 to 1:2, more preferably from 1:0.7 to 1:1.5 and most preferably from 1:0.8 to 1:1.2.

Alternatively, in cabozantinib phosphate Form A, the molar ratio of the cabozantinib relative to the combined content of dihydrogenphosphate and hydrogenphosphate is in the range of from 1:0.5 to 1:2, more preferably from 1:0.7 to 1:1.5 and most preferably from 1:0.8 to 1:1.2.

Cabozantinib Hydrochloride Form A-1

WO2010/083414 discloses a cabozantinib hydrochloride salt which shows hydrate formation and a phase change upon exposure to high humidity and high temperature. It was thus surprising that an anhydrous and non-hygroscopic form of cabozantinib hydrochloride could be prepared.

The present invention therefore also relates to cabozantinib hydrochloride Form A-1. Preferably, cabozantinib hydrochloride Form A-1 can be characterized by having a XRPD comprising reflections at 2-Theta angles of (12.7±0.2)°, (20.7±0.2)°, (24.2±0.2)°, (25.4±0.2)° when measured at 20° C. with Cu-Kalpha radiation having a wavelength of 0.15419 nm.

More preferably, Form A-1 can be characterized by having a XRPD comprising reflections at 2-Theta angles of (12.7±0.2)°, (18.0±0.2)°, (20.7±0.2)°, (24.2±0.2)°, (25.4±0.2)°, when measured at 20° C. with Cu-Kalpha radiation having a wavelength of 0.15419 nm.

Still further, cabozantinib hydrochloride Form A-1 can be characterized by having the XRPD comprising additional reflections at one or more, such as two, three, four or five, 2-Theta angles selected from the group of (6.9±0.2)°, (7.9±0.2)°, (11.2±0.2)°, (14.2±0.2)°, (14.7±0.2)°, (15.7±0.2)°, (18.6±0.2)°, (23.2±0.2)°, (29.0±0.2)°, when measured at 20° C. with Cu-Kalpha radiation having a wavelength of 0.15419 nm. Hence, the crystalline form Form A-1 can be characterized by having the XRPD comprising additional one or more, such as two, three, four, five, or even all of the reflections at 2-Theta angles selected from the group of reflections marked as bold in Table 1-second column, the XRPD when measured at 20° C. with Cu-Kalpha radiation having a wavelength of 0.15419 nm, in particular as disclosed in reference example A) herein.

Still further, cabozantinib hydrochloride Form A-1 is characterized by having the XRPD comprising additional reflections at one or more, such as two, three, four or five, 2-Theta angles selected from the group of (7.1±0.2)°, (8.9±0.2)°, (9.4±0.2)°, (11.6±0.2)°, (11.9±0.2)°, (13.4±0.2)°, (16.3±0.2)°, 17.2±0.2)°, (19.3±0.2)°, (20.0±0.2)°, (21.3±0.2)°, (21.9±0.2)°, (22.3±0.2)°, (22.8±0.2)°, (23.6±0.2)°, (26.4±0.2)°, (27.5±0.2)°, (29.9±0.2)°, when measured at 20° C. with Cu-Kalpha radiation having a wavelength of 0.15419 nm.

Alternatively, cabozantinib hydrochloride Form A-1 can be characterized by showing a XRPD comprising peaks at all of the positions shown in bold in Table 1-second column, when measured at 20° C. with Cu-Kalpha radiation having a wavelength of 0.15419 nm. Alternatively, cabozantinib hydrochloride Form A-1 can be characterized by having a XRPD comprising all reflections listed in Table 1-second column, when measured at 20° C. with Cu-Kalpha radiation having a wavelength of 0.15419 nm. Alternatively, cabozantinib hydrochloride Form A-1 can be characterized by showing a XRPD essentially the same as displayed in FIG. 2 of the present invention, when measured at 20° C. with Cu-Kalpha radiation having a wavelength of 0.15419 nm.

Additionally or alternatively, cabozantinib hydrochloride Form A-1 can be characterized by having a TG/DTA curve showing a weight loss of at most 1.0%, preferably at most 0.8%, more preferably the weight loss is in the range of from 0.2 to 0.7 weight-%, based on the weight of cabozantinib hydrochloride Form A-1, when measured at a temperature in the range of from 25 to 200° C. and a heating rate of about 10° C./min. Additionally or alternatively, cabozantinib hydrochloride Form A-1 can be characterized by having a TG/DTA curve showing a weight loss equal or less than 0.7 weight-%, equal or less than 0.6 weight-%, equal or less than 0.5 weight-% or equal or less than 0.4 weight-%, based on the weight of the crystalline Form 1-1 when measured as disclosed in reference example B) herein.

Figure 4:
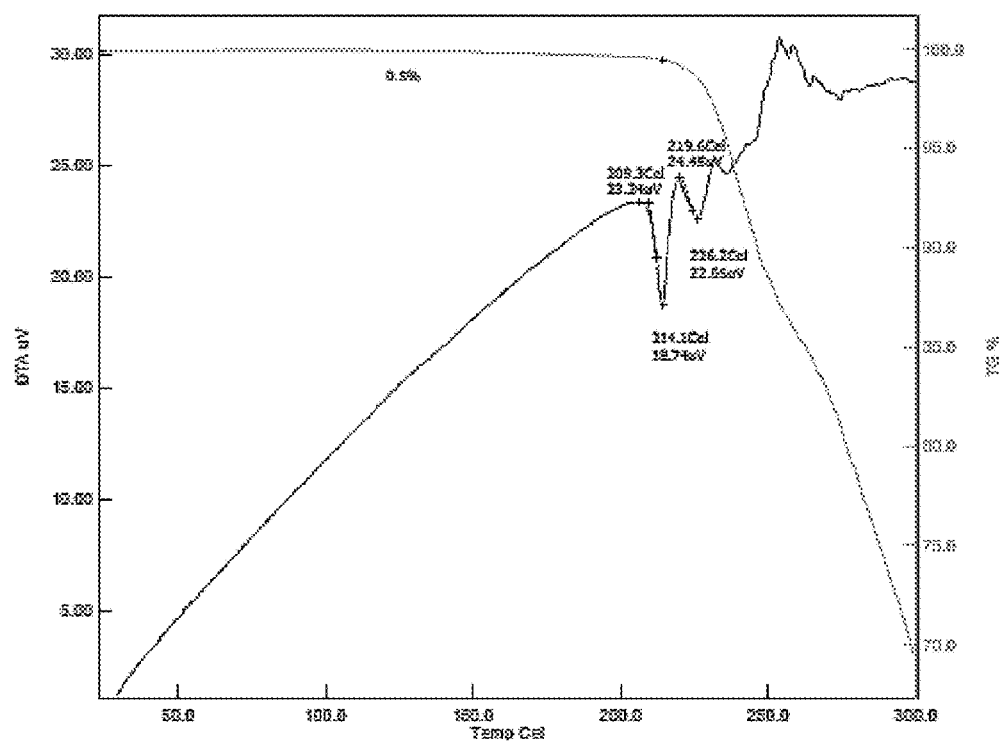
FIG. 4: Representative TG/DTA curve of the crystalline Form A-1 of cabozantinib hydrochloride from ethanol according to the present invention.

Additionally or alternatively, cabozantinib hydrochloride Form A-1 can be characterized by having a TG/DTA curve as disclosed in FIG. 4, in particular as measured as disclosed in reference example B) herein.

Alternatively or additionally, cabozantinib hydrochloride Form A-1 can be characterized by having a water content of at most 1.0%, such as at most 0.5%, preferably equal or less than 0.3 weight-% when determined by KF analysis in particular as measured as disclosed in reference example F) herein, in particular as disclosed in reference example F) herein.

Alternatively or additionally, cabozantinib hydrochloride Form A-1 can be characterized as being an anhydrous crystalline form and most preferably a non-solvated and anhydrous crystalline form.

Alternatively or additionally, cabozantinib hydrochloride Form A-1 can be characterized as being non-hygroscopic.

Preferably, cabozantinib hydrochloride Form A-1 is provided in substantially pure form.

Preferably, cabozantinib hydrochloride Form A-1 has substantially pure phase homogeneity as indicated by less than 10%, preferably less than 5%, and more preferably less than 2% of the total peak area in the experimentally measured XRPD pattern arising from the extra peaks that are absent from the simulated XRPD pattern. Most preferred is a crystalline form of cabozantinib hydrochloride Form A-1 having substantially pure phase homogeneity with less than 1% of the total peak area in the experimentally measured XRPD pattern arising from the extra peaks that are absent from the simulated XRPD pattern. In the present context the term "extra peaks" refers to XRPD peaks that do not belong or are not assigned to Form A-1

In one embodiment, a composition is provided consisting essentially of the cabozantinib hydrochloride Form A-1. The composition of this embodiment may comprise at least 90 weight % of cabozantinib hydrochloride Form A-1, based on the weight of cabozantinib hydrochloride in the composition. The composition comprises preferably at least 95 weight-% of cabozantinib hydrochloride Form A-1, more preferably at least 97 weight-% of cabozantinib hydrochloride Form A-1, even more preferably at least 99 weight-% of cabozantinib hydrochloride Form A-1, based on the weight of cabozantinib hydrochloride in the composition.

Preferably, in cabozantinib hydrochloride Form A-1, the molar ratio of the cabozantinib relative to the hydrochloride is in the range of from 1:0.5 to 1:2, more preferably from 1:0.7 to 1:1.5 and most preferably from 1:0.8 to 1:1.2.

Preparation of Cabozantinib Salts and Crystalline Forms Thereof

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

Crystals of drugs, including polymorphs, methods of preparation, and characterization of drug crystals are discussed in Solid-State Chemistry of Drugs, S. R. Byrn, R. R. Pfeiffer, and J. G. Stowell, 2nd Edition, SSCI, West Lafayette, Ind. (1999).

The present invention also relates to a process for the preparation of the novel crystalline form of cabozantinib phosphate Form A and the novel crystalline form of cabozantinib hydrochloride Form A-1, all as disclosed above. The process comprises
(1) crystallizing N-{4-[(6,7-dimethoxy-4-quinolinyl)oxy]phenyl}-N'-(4-fluorophenyl)-1,1-cyclopropanedicarboxamide phosphate or N-{4-[(6,7-dimethoxy-4-quinolinyl)oxy]phenyl}-N'-(4-fluorophenyl)-1,1-cyclopropanedicarboxamide hydrochloride in a solvent comprising a $C_1$-$C_4$ alcohol, obtaining the crystalline cabozantinib phosphate Form A or cabozantinib hydrochloride Form A-1 of the invention as disclosed above;
(2) optionally drying the crystalline form obtained from (1).

For example the process may comprise
(1) crystallizing N-{4-[(6,7-dimethoxy-4-quinolinyl)oxy]phenyl}-N'-(4-fluorophenyl)-1,1-cyclopropanedicarboxamide phosphate or N-{4-[(6,7-dimethoxy-4-quinolinyl)oxy]phenyl}-N'-(4-fluorophenyl)-1,1-cyclopropanedicarboxamide hydrochloride in a solvent consisting of a $C_1$-$C_4$ alcohol, obtaining the crystalline cabozantinib phosphate Form A or cabozantinib hydrochloride Form A-1 of the invention as disclosed above, wherein the crystallizing is carried out at a temperature of from 10° C. to 50° C.;
(2) optionally drying the crystalline form obtained from (1).

The resulting cabozantinib phosphate Form A or cabozantinib hydrochloride Form A-1 are as described above.

Hence, in one alternative, the present invention is directed to a process for the preparation of crystalline Form A of N-{4-[(6,7-dimethoxy-4-quinolinyl)oxy]phenyl}-N'-(4-fluorophenyl)-1,1-cyclopropanedicarboxamide phosphate (cabozantinib phosphate) as disclosed above comprising
(1-1) crystallizing N-{4-[(6,7-dimethoxy-4-quinolinyl)oxy]phenyl}-N'-(4-fluorophenyl)-1,1-cyclopropanedicarboxamide phosphate (cabozantinib phosphate) in a solvent comprising a $C_1$-$C_4$ alcohol, obtaining the crystalline Form A as disclosed above;
(2-1) optionally drying the crystalline form obtained from (1-1).

For example, the process may comprise
(1-1) crystallizing N-{4-[(6,7-dimethoxy-4-quinolinyl)oxy]phenyl}-N'-(4-fluorophenyl)-1,1-cyclopropanedicarboxamide phosphate (cabozantinib phosphate) in a solvent consisting of a $C_1$-$C_4$ alcohol, obtaining the crystalline Form A as disclosed above, wherein the crystallizing is carried out at a temperature of from 10° C. to 50° C.;
(2-1) optionally drying the crystalline form obtained from (1-1).

Hence, in another alternative the present invention is directed to a process for the preparation of the crystalline Form A-1 of N-{4-[(6,7-dimethoxy-4-quinolinyl)oxy]phenyl}-N'-(4-fluorophenyl)-1,1-cyclopropanedicarboxamide hydrochloride as disclosed above comprising
(1-2) crystallizing N-{4-[(6,7-dimethoxy-4-quinolinyl)oxy]phenyl}-N'-(4-fluorophenyl)-1,1-cyclopropanedicarboxamide hydrochloride salt in a solvent comprising a $C_1$-$C_4$ alcohol, obtaining the crystalline Form A-1 as disclosed above;
(2-2) optionally drying the crystalline form of (1-2).

For example, the process may comprise
(1-2) crystallizing N-{4-[(6,7-dimethoxy-4-quinolinyl)oxy]phenyl}-N'-(4-fluorophenyl)-1,1-cyclopropanedicarboxamide hydrochloride salt in a solvent consisting of a $C_1$-$C_4$ alcohol, obtaining the crystalline Form A-1 as disclosed above, wherein the crystallizing is carried out at a temperature of from 10° C. to 50° C.;
(2-2) optionally drying the crystalline form of (1-2).

In the above method to prepare crystals, a compound can be suspended and/or stirred in the solvent to afford a slurry. The term "slurry", as used herein, means a saturated solution of the compound, which may also contain an additional amount of the compound to afford a heterogeneous mixture of the compound and a solvent at a given temperature.

Alternatively, the hydrochloride salt or the phosphate salt formation and the crystallization thereof to cabozantinib hydrochloride Form A-1 or cabozantinib phosphate Form A may be carried out in one step. In this case, step (1) or (1-2) is the following step (1'), (1') dissolving N-{4-[(6,7-dimethoxy-4-quinolinyl)oxy]phenyl}-N'-(4-fluorophenyl)-1,1-cyclopropanedicarboxamide in a solvent selected from a $C_1$-$C_4$ alcohol, obtaining a mixture and treating said mixture with hydrochloric acid (HCl) or phosphoric acid, preferably hydrochloric acid (HCl), obtaining crystalline cabozantinib hydrochloride Form A-1 or crystalline cabozantinib phosphate Form A, as disclosed above.

Cabozantinib free base is typically used as the starting material. Cabozantinib free base can, for example, be prepared according to WO 2005/030140, preparative example 48, or WO 2010/083414, preparative example 1.6.

Preferably, the $C_1$-$C_4$ alcohol in (1) or (1-1) or (1-2) or (1') is selected from methanol, ethanol, 1-propanol, 2-propanol, 1-butanol, 2-butanol, isobutanol, tert-butanol, or mixtures of two or more thereof, more preferably the alcohol in (1) or (1-1) or (1-2) or (1') is selected from methanol or ethanol.

Preferably, to obtain crystalline cabozantinib phosphate Form A, the solvent of (1) or (1-1) or (1') comprises or consists of methanol.

Preferably, to obtain crystalline cabozantinib hydrochloride Form A-1, the solvent of (1) or (1-2) or (1') comprises or consists of ethanol.

Preferably, (1) or (1-1) or (1-2) or (1') is carried out at a temperature in the range of from 10° C. to 50° C., more preferably at a temperature in the range of from 15° C. to 45° C.

Preferably, (1) or (1-1) or (1-2) or (1') are effected by temperature cycling. The temperature cycling of (1) or (1-1) or (1-2) or (1') is preferably carried out at a temperature in the range of from 20 to 45° C. Each cycle is preferably carried out for a period in the range of 2 to 5 h, preferably of from 3 to 4 h. The temperature cycling is preferably carried out for an overall time of 2 to 4 days, preferably 3 days. The cooling rate between hold periods is preferably of 1° C./min. Preferably, the temperature cycling is carried out while stirring.

Preferably, the molar ratio of the cabozantinib of (1) or (1-1) or (1') relative to phosphorous in (1) or (1-1) or (1') is in the range of from 1:0.5 to 1:2, more preferably in the range of from 1:0.7 to 1:1.5 and most preferably in the range of from 1:0.8 to 1:1.2.

Preferably, the molar ratio of the cabozantinib in (1) or (1-2) or (1') relative to hydrochloric acid is in the range of from 1:0.5 to 1:2, more preferably in the range of from 1:0.7 to 1:1.5 and most preferably in the range of from 1:0.8 to 1:1.2.

Seed crystals may be added in (1) or (1-1) or (1-2) or (1'). The seed crystals are preferably cabozantinib phosphate Form A or cabozantinib hydrochloride Form A-1.

Seed crystals may be added to a crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, Chemical Engineering Science, 1971, 26, 369-377.

In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

The process as disclosed above, after (1) or (1-1) or (1-2) or (1'), may further comprise (1-i) optionally isolating at least a part of the crystalline form obtained from (1) or (1-1) or (1-2) or (1') from its mother liquor;
(1-ii) optionally washing the isolated crystalline form obtained from (1-i) with a solvent.

The crystalline cabozantinib phosphate Form A obtained from (1) or (1-1) or the crystalline cabozantinib hydrochloride Form A-1 of (1) or (1-2) or (1') may optionally be isolated in (1-i) by any conventional method such as filtration or centrifugation, most preferably by filtration.

Optionally, the isolated cabozantinib phosphate Form A or cabozantinib hydrochloride Form A-1 obtained from (1-i) may be washed with a solvent. Preferably, the solvent is a $C_1$-$C_4$ alcohol as defined for step (1) or (1-1) or (1-2) or (1'), preferably is the same alcohol used in step (1) or (1-1) or (1-2) or (1').

The isolated crystalline cabozantinib phosphate Form A or cabozantinib hydrochloride Form A-1 may optionally be dried (in (2)) at a temperature of about 40° C. or less, for example at about room temperature. Drying may be performed for a period in the range of from about 1 to 72 hours, preferably from about 2 to 48 hours, more preferably from about 4 to 24 hours and most preferably from about 6 to 18 hours. Drying may be performed under vacuum preferably at about 100 mbar or less, more preferably at about 50 mbar or less and most preferably at about 30 mbar or less, for example at about 20 mbar or less.

Additionally or alternatively, the starting salt to be crystallized in any one of (1), (1-1), (1-2) is obtained by a process similar to the one described in WO2010/083414. Briefly, cabozantinib free base, for example prepared according to WO 2010/083414, preparative example 1.6., can be dissolved or slurried in a solvent such as acetone. The phosphoric acid or the hydrochloride acid can be dissolved or slurried in a solvent such as tetrahydrofuran. The two solutions/slurries are then combined together.

The resulting mixture is then preferably subjected to temperature cycling. The temperature cycling is preferably carried out at a temperature in the range of from 20 to 45° C. Each cycle is preferably carried out for a period in the range of 2 to 5 h, more preferably of from 3 to 4 h. The temperature cycling is preferably carried out for an overall time of 2 to 4 days, preferably 3 days. The cooling rate between hold periods is preferably of 1° C./min. Preferably, the temperature cycling is carried out while stirring. Solid cabozantinib hydrochloride or solid cabozantinib phosphate is obtained that is different from cabozantinib hydrochloride form A-1 or cabozantinib phosphate form A of the present invention. However, the so obtained solid material is a suitable starting material for the processes of the present invention and can therefore be used for (1), (1-1) and (1-2), respectively.

Pharmaceutical Composition, Use and Therapy

The cabozantinib phosphate Form A of the present invention may be used alone or in combination, or formulated with one or more excipients or other active pharmaceutical ingredients to provide formulations suitable for the treatment of the indications identified above.

Likewise, the cabozantinib hydrochloride Form A-1 of the present invention may be used alone or in combination, or formulated with one or more excipients or other active pharmaceutical ingredients to provide formulations suitable for the treatment of the indications identified above.

The present invention is directed to pharmaceutical compositions comprising cabozantinib phosphate Form A or cabozantinib hydrochloride Form A-1 all as defined above and at least a pharmaceutically acceptable excipient.

More preferably, the pharmaceutical composition of the invention comprises cabozantinib phosphate Form A.

The pharmaceutical composition of the invention is preferably an oral dosage form such as tablet, capsule such as hard gelatin capsule, syrup, preferably the oral dosage form is a tablet or a capsule, preferably the capsule is a hard gelatin capsule.

Preferably the pharmaceutical composition comprises an effective dose of a crystalline form of the invention. Preferably, the effective dose is in the range of 20 to 80 mg of the crystalline form of the invention. The effective dose preferably refers to a daily dose.

The pharmaceutical composition of the invention, preferably as an oral dosage form, comprises an effective amount of cabozantinib phosphate Form A or cabozantinib hydrochloride Form A-1 and one or more pharmaceutically acceptable excipients such as filler, disintegrant, glidant, lubricant, binder; preferably the oral dosage form of the invention comprises an effective amount of cabozantinib phosphate Form A or cabozantinib hydrochloride Form A-1, filler, disintegrant, glidant and lubricant.

A preferred oral dosage is a capsule comprising an effective amount of cabozantinib phosphate Form A or cabozantinib hydrochloride Form A-1, a filler, a disintegrant, a glidant and a lubricant. Preferably the filler is a silicified microcrystalline cellulose, preferably the disintegrant is croscarmellose sodium or sodium starch glycolate or mixture thereof, preferably the glidant is silica colloidal anhydrous, and preferably the lubricant is stearic acid. Preferably the empty capsule is of gelatin and optionally comprises colorants, opacifier and ink. Black iron oxide and red iron oxide are examples of colorants according to the invention. Titanium dioxide can be used as opacifier.

Further, the present invention relates to cabozantinib phosphate Form A or cabozantinib hydrochloride Form A-1 of the invention or to the pharmaceutical composition comprising cabozantinib phosphate Form A or cabozantinib hydrochloride Form A-1 for use as a medicament, preferably as an anti-cancer medicament.

Further, the present invention relates to cabozantinib phosphate Form A or cabozantinib hydrochloride Form A-1 of the invention or to the pharmaceutical composition comprising cabozantinib phosphate Form A or cabozantinib hydrochloride Form A-1 for use in the treatment or prevention of cancer, preferably of a thyroid cancer, wherein preferably the thyroid cancer is a metastatic medullary thyroid cancer.

Advantages

The TG/DTA analysis of cabozantinib phosphate form A of the present invention (see FIG. 3) showed a weight loss of less than ca. 0.3 weight-% based on the weight of the crystalline form before the TG/DTA analysis. KF analysis of the water content of Form A of the present invention gave a result of 0.5 weight-%. Hence, advantageously, Form A is substantially an anhydrous crystalline salt. By contrast, patent application WO2010/083414 discloses a cabozantinib phosphate salt that shows a 8 weight-% gain due to water absorption.

The TG/DTA analysis of cabozantinib hydrochloride Form A-1 of the present invention (see FIG. 4) showed a weight loss of about 0.5-0.7 weight-% based on the weight of the crystalline form before the TG/DTA analysis. KF analysis of the water content of cabozantinib hydrochloride Form A-1 of the present invention gave a result of about 0.2 weight-%. Advantageously, Form A-1 is a substantially anhydrous crystalline salt. By contrast, patent application WO2010/083414 discloses a cabozantinib hydrochloride salt which is hygroscopic.

Table 2 summarizes the aforementioned data:

TABLE 2

Physicochemical properties of cabozantinib phosphate Form A and cabozantinib hydrochloride Form A-1 of the invention

| Analytical Method | Cabozantinib phosphate Form A (present invention) | Cabozantinib hydrochloride Form A-1 (present invention) |
| --- | --- | --- |
| TG/DTA | 0.3 weight-% of weight loss below ca. 210° C. | 0.5 weight-% of weight loss below ca. 215° C. |
| KF analysis water content | 0.5 weight-% | 0.2 weight-% |
| Aqueous Solubility | 0.09 mg/ml | 0.21 mg/ml |
| Water absorption | 1% | 0.07% |

Figure 5:
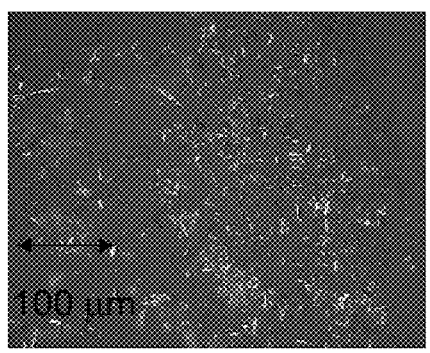
FIG. 5: Representative PLM analysis of Form A of cabozantinib phosphate of the present invention in polarized and non polarized light showing rod-like crystals.
Figure 5:
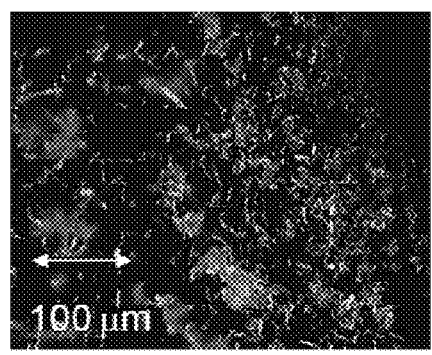

Cabozantinib phosphate Form A comprises crystals having rod-like-shaped morphology (FIG. 5). It shows improved filterability. Rod-shaped crystals are highly appreciated by formulation scientists as they usually show good powder properties such as flow properties and compressibility and are therefore easy to handle in pharmaceutical processes.

Figure 6:
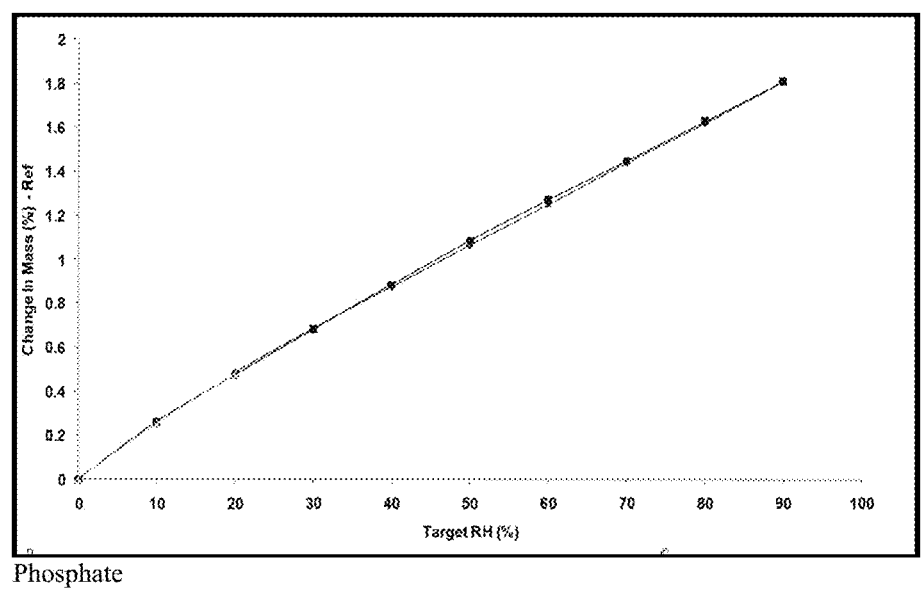
FIG. 6: Representative DVS curve of the crystalline Form A of cabozantinib phosphate according to the present invention.
Figure 7:
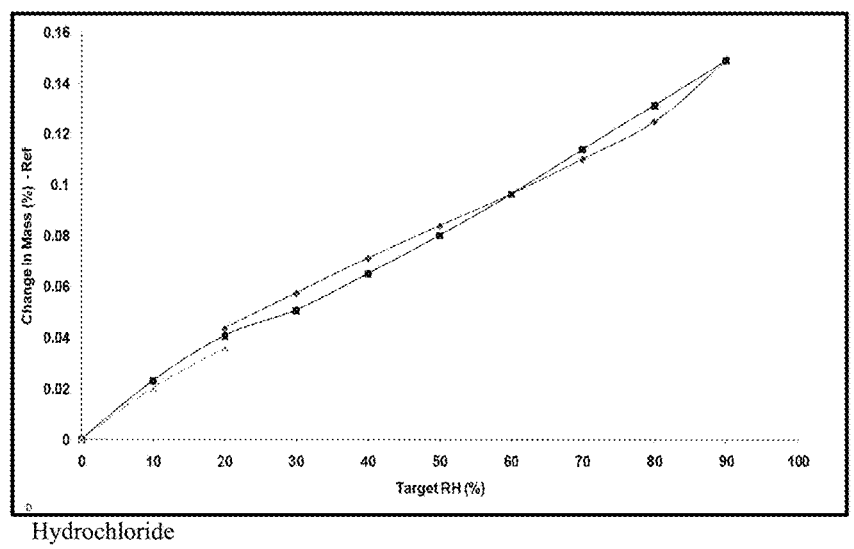
FIG. 7: Representative DVS curve of the crystalline Form A-1 of cabozantinib hydrochloride from ethanol according to the present invention.

Cabozantinib phosphate Form A comprises crystals which absorb only 1 weight-% water in a DVS between 20% r.h. and 70 weight-% r.h. (FIG. 6). Cabozantinib hydrochloride Form A-1 comprises crystals which absorb only 0.07 weight-% water in a DVS between 20% r.h. and 70% r.h. (FIG. 7). Non-hygroscopic crystals are highly appreciated by formulation scientists as they usually are easy to handle in pharmaceutical processes and compatible with numerous formulation processes.

All in all cabozantinib phosphate Form A and cabozantinib hydrochloride Form A-1 show beneficial physicochemical properties, which render them particular suitable crystalline forms of cabozantinib for pharmaceutical purposes. Especially their low interaction with water vapour (non hygroscopicity) is beneficial for the use of these forms for pharmaceutical formulation processes. Both forms further show a morphology which is beneficial for the use of these forms for pharmaceutical formulation processes.

The present invention is further illustrated by the following embodiments and combinations of embodiments resulting from the given dependencies and back-references:

0. A crystalline form of N-{4-[(6,7-dimethoxy-4-quinolinyl)oxy]phenyl}-N'-(4-fluorophenyl)-1,1-cyclopropanedicarboxamide (cabozantinib) phosphate.
1. A crystalline form of N-{4-[(6,7-dimethoxy-4-quinolinyl)oxy]phenyl}-N'-(4-fluorophenyl)-1,1-cyclopropanedicarboxamide (cabozantinib) phosphate characterized by a powder X-ray diffractogram (XRPD) comprising reflections at 2-Theta angles of (6.0±0.2)°, (9.7±0.2)° and (12.0±0.2)°, when measured at 20° C. with Cu-Kalpha radiation having a wavelength of 0.15419 nm, in particular as disclosed in reference example A) herein.
2. The crystalline form of embodiment 0 or 1 characterized by the XRPD comprising reflections at 2-Theta angles of (6.0±0.2)°, (9.7±0.2)°, (12.0±0.2)° and (19.4±0.2)°, when measured at 20° C. with Cu-Kalpha radiation having a wavelength of 0.15419 nm, in particular as disclosed in reference example A) herein.
3. The crystalline form of any one of embodiments 0 or 1 to 2 characterized by the XRPD comprising reflections at 2-Theta angles of (6.0±0.2)°, (9.7±0.2)°, (12.0±0.2)°, (19.4±0.2)°, (25.1±0.2)°, when measured at 20° C. with Cu-Kalpha radiation having a wavelength of 0.15419 nm, in particular as disclosed in reference example A) herein.
4. The crystalline form of any one of embodiments 1 to 3, characterized by having an XRPD comprising additional one or more reflections at 2-Theta angles selected from the group of (14.1-0.2)°, (14.5±0.2)°, (23.6±0.2)°, (24.2±0.2)°, (25.1±0.2)°, when measured at 20° C. with Cu-Kalpha radiation having a wavelength of 0.15419 nm, in particular as disclosed in reference example A) herein.
5. The crystalline salt of any one of embodiments 0, or 1 to 4, characterized by having an XRPD comprising further five or more reflections at 2-Theta angles selected from the group of (15.7±0.2)°, (16.2±0.2)°, (16.6±0.2)°, (17.7±0.2)°, (20.0±0.2)°, (21.5±0.2)°, (24.7±0.2)°, (26.7±0.2)°, (27.0±0.2)° and (28.4±0.2)°, when measured at 20° C. with Cu-Kalpha radiation having a wavelength of 0.15419 nm, in particular as disclosed in reference example A) herein.
6. The crystalline form of any one of embodiments 1 to 5, characterized by having a XRPD comprising all reflections marked as bold in Table 1-first column, when measured at 20° C. with Cu-Kalpha radiation having a wavelength of 0.15419 nm, in particular as disclosed in reference example A) herein.
7. The crystalline form of any one of embodiments 0, or 1 to 6, characterized by a XRPD comprising all reflections listed in Table 1-first column, when measured at 20° C. with Cu-Kalpha radiation having a wavelength of 0.15419 nm, in particular as disclosed in reference example A) herein.
8. The crystalline form of any one of embodiments 0, or 1 to 7, characterized by an XRPD being essentially the same as displayed in FIG. 1, when measured at 20° C. with Cu-Kalpha radiation having a wavelength of 0.15419 nm, in particular as disclosed in reference example A) herein.
9. The crystalline form of any one of embodiments 0 or 1 to 8, characterized by having a TG/DTA curve showing a weight loss of at most 1.0 weight-% based on the weight of the crystalline form, in particular when measured according to reference example B) herein.
10. The crystalline form of embodiment 9, wherein the weight loss is at most 0.5 weight-% based on the weight of the crystalline form, preferably in the range of from 0.2 to 0.4 weight-%, in particular when measured according to reference example B) herein.
11. The crystalline form of any one of embodiments 0 or 1 to 10 characterized by having a TG/DTA curve being essentially the same as displayed in FIG. 3 when measured at a heating rate of 10° C./min, in particular as disclosed in reference example B) herein.
12. The crystalline form of any one of embodiments 0 or 1 to 11 characterized by having a water content of at most 1.0 weight-%, such as in the range from 0.1 to 0.7 weight-%, based on the weight of the crystalline form, as determined by KF, in particular as disclosed in reference example F) herein.
13. The crystalline form of embodiment 12, wherein the water content is in the range of from 0.4 to 0.6 weight-% based on the weight of the crystalline form as determined by KF, in particular as disclosed in reference example F) herein.
14. The crystalline form of any one of the embodiments 0 or 1 to 13, wherein the molar ratio of N-{4-[(6,7-dimethoxy-4-quinolinyl)oxy]phenyl}-N'-(4-fluorophenyl)-1,1-cyclopropanedicarboxamide relative to phosphorous is in the range of from 1:0.5 to 1:2, more preferably of from 1:0.7 to 1:1.5 and most preferably of from 1:0.8 to 1:1.2.
0' A crystalline form of N-{4-[(6,7-dimethoxy-4-quinolinyl)oxy]phenyl}-N'-(4-fluorophenyl)-1,1-cyclopropanedicarboxamide hydrochloride.
15. A crystalline form of N-{4-[(6,7-dimethoxy-4-quinolinyl)oxy]phenyl}-N'-(4-fluorophenyl)-1,1-cyclopropanedicarboxamide hydrochloride characterized by a XRPD comprising reflections at 2-Theta angles of (12.7±0.2)°, (20.7±0.2)°, (24.2±0.2)° and (25.4±0.2)°, when measured at 20° C. with Cu-Kalpha radiation having a wavelength of 0.15419 nm, in particular as disclosed in reference example A) herein.
16. The crystalline form of embodiment 0' or 15, characterized by a XRPD comprising reflections at 2-Theta angles of (12.7±0.2)°, (18.0±0.2)°, (20.7±0.2)°, (24.2±0.2)°, (25.4±0.2)°, when measured at 20° C. with Cu-Kalpha radiation having a wavelength of 0.15419 nm, in particular as disclosed in reference example A) herein.
17. The crystalline form of embodiment 0' or 15 or 16, characterized by having a XRPD comprising additional one or more reflections at 2-Theta angles selected from the group of reflections marked as bold in Table 1-second column, the XRPD when measured at 20° C. with Cu-Kalpha radiation having a wavelength of 0.15419 nm, in particular as disclosed in reference example A) herein.
18. The crystalline form of any one of embodiments 0' or 15 to 17, characterized by having a XRPD comprising all reflections marked as bold in Table 1-second column, the XRPD when measured at 20° C. with Cu-Kalpha radiation having a wavelength of 0.15419 nm, in particular as disclosed in reference example A) herein.
19. The crystalline form of any one of embodiments 0' or 15 to 18, characterized by having a XRPD comprising all reflections listed in Table 1-second column, when measured at 20° C. with Cu-Kalpha radiation having a wavelength of 0.15419 nm, in particular as disclosed in reference example A) herein.
20. The crystalline form of any one of embodiments 0' or 15 to 18, characterized by a XRPD being essentially the same as displayed in FIG. 2, when measured at 20° C. with Cu-Kalpha radiation having a wavelength of 0.15419 nm, in particular as disclosed in reference example A) herein.
21. The crystalline form of any one of embodiments 0' or 15 to 20, characterized by having a TG/DTA curve showing a weight loss equal or less than 1 weight-% based on the weight of the crystalline form when measured as disclosed in reference example B) herein.
22. The crystalline form of embodiment 21, wherein the weight loss is in the range of from 0.2 to 0.7 weight-% based on the weight of the crystalline form when measured as disclosed in reference example B) herein.
23. The crystalline form of embodiment 21 or 22, wherein the weight loss is equal or less than 0.7 weight-%, equal or less than 0.6 weight-% or equal or less than 0.5 weight-%, based on the weight of the crystalline form when measured as disclosed in reference example B) herein.

24. The crystalline form of any one of embodiments 0' or 15 to 23, characterized by having a TG/DTA curve being essentially the same as displayed in FIG. 4, when measured as disclosed in reference example B) herein.

25. The crystalline form of any one of embodiments 0' or 15 to 24, characterized by having a water content of at most 1.0 weight-% based on the weight of the crystalline form when determined by KF, in particular as disclosed in reference example F) herein.

26. The crystalline form of embodiment 25, wherein the water content is equal or less than 0.3 weight-% based on the weight of the crystalline form when determined by KF, in particular as disclosed in reference example F) herein.

27. The crystalline form of any one of embodiments 0' or 15 to 26, wherein the molar ratio of N-{4-[(6,7-dimethoxy-4-quinolinyl)oxy]phenyl}-N'-(4-fluorophenyl)-1,1-cyclopropanedicarboxamide relative to chloride is in the range of from 1:0.5 to 1:2, more preferably from about 1:0.6 to 1:1.5 and most preferably from 1:0.8 to 1:1.

28. A process for the preparation of the crystalline form according to any one of embodiments 1 to 27, preferably according to any one of embodiments 1 to 14 comprising:
    (1) crystallizing N-{4-[(6,7-dimethoxy-4-quinolinyl)oxy]phenyl}-N'-(4-fluorophenyl)-1,1-cyclopropanedicarboxamide phosphate or N-{4-[(6,7-dimethoxy-4-quinolinyl)oxy]phenyl}-N'-(4-fluorophenyl)-1,1-cyclopropanedicarboxamide hydrochloride in a solvent comprising an a $C_1$-$C_4$ alcohol, obtaining the crystalline form according to any one of embodiments 1 to 27, preferably according to any one of embodiments 1 to 14;
    (2) optionally drying the crystalline form obtained from (1), obtaining the crystalline form according to any one of embodiments 1 to 27, preferably according to any one of embodiments 1 to 14.

29. A process for the preparation of a crystalline form of N-{4-[(6,7-dimethoxy-4-quinolinyl)oxy]phenyl}-N'-(4-fluorophenyl)-1,1-cyclopropanedicarboxamide phosphate according to any one of embodiments 1 to 14 comprising
    (1-1) crystallizing N-{4-[(6,7-dimethoxy-4-quinolinyl)oxy]phenyl}-N'-(4-fluorophenyl)-1,1-cyclopropanedicarboxamide phosphate in a solvent comprising an alcohol, preferably a $C_1$-$C_4$ alcohol, obtaining the crystalline form of any one of embodiments 1 to 14;
    (2-1) optionally drying the crystalline form obtained from (1-1) obtaining the crystalline form of any one of embodiments 1 to 14.

30. A process for the preparation of a crystalline form of N-{4-[(6,7-dimethoxy-4-quinolinyl)oxy]phenyl}-N'-(4-fluorophenyl)-1,1-cyclopropanedicarboxamide hydrochloride according to any one of embodiments 15 to 27, comprising
    (1-2) crystallizing N-{4-[(6,7-dimethoxy-4-quinolinyl)oxy]phenyl}-N'-(4-fluorophenyl)-1,1-cyclopropanedicarboxamide hydrochloride in a solvent comprising an alcohol, preferably a $C_1$-$C_4$ alcohol, obtaining the crystalline form of any one of embodiments 15 to 27;
    (2-2) optionally drying the crystalline form obtained from (1-2) of any one of embodiments 15 to 27.

31. The process of any one of embodiments 28 to 30, wherein the solvent in (1) or (1-1) or (1-2) consists of a $C_1$-$C_4$ alcohol.

32. The process of any one of embodiments 28 to 31, wherein the $C_1$-$C_4$ alcohol is selected from methanol, ethanol, 1-propanol, 2-propanol, 1-butanol, 2-butanol, isobutanol, tert-butanol, or mixtures of two or more thereof, preferably from methanol or ethanol.

33. The process of any one of embodiments 28 to 29 or 31 to 32, wherein the $C_1$-$C_4$ alcohol is methanol and the crystalline form is the crystalline form of any one of embodiments 1 to 14.

34. The process of any one of embodiments 28 or 30 to 32, wherein the $C_1$-$C_4$ alcohol is ethanol and the crystalline form is the crystalline form of any one of embodiments 15 to 27.

35. The process of any one of embodiments 28 to 34, wherein step (1) or (1-1) or (1-2) is carried out at a temperature in the range of from 10° C. to 50° C., preferably of from 15° C. to 45° C.

36. The process of any one of embodiments 28 to 35, wherein the process after (1) or (1-1) or (1-2) further comprises
    (1-i) isolating at least a part of the crystalline form of (1) or (1-1) or (1-2) from its mother liquor;
    (1-ii) optionally washing the isolated crystalline form of (1-i) with a solvent, preferably a $C_1$-$C_4$ alcohol.

37. The process of any one of embodiments 28 to 36, wherein isolating in (1-i) is by a method selected from filtration or centrifugation, most preferably by filtration.

38. The process of any one of embodiments 28 to 37, wherein in (1-i) the solvent is a $C_1$-$C_4$ alcohol as defined in embodiment 31 or 32, preferably the $C_1$-$C_4$ alcohol is the same $C_1$-$C_4$ alcohol used in step (1) or (1-1) or (1-2).

39. The process of any one of embodiments 28 to 38, wherein the drying in (2), or (2-1) or (2-2) is at a temperature of about 40° C. or less for example at about room temperature.

40. The process of any one of embodiments 28 to 39, wherein step (1) or (1-1) or (1-2) is carried out under conditions of temperature cycling.

41. The process of embodiment 40, wherein temperature cycling is within the range of from 20 to 45° C.

42. The process of embodiment 40 or 41, wherein the temperature cycling is carried out with a period in the range of 2 to 5 h, preferably of from 3 to 4 h.

43. The process of any one of embodiments 40 to 42, wherein the temperature cycling is carried out for an overall time of 2 to 4 days, preferably 3 days.

44. The process of any one of embodiments 40 to 43, wherein the temperature cycling is carried out with hold periods, wherein the cooling rate between hold periods is preferably of 1° C./min.

45. The process of any one of embodiments 28 to 29 or 31 to 44, wherein the crystalline form obtained in (1) or (1-1) or (2) or (2-1) is characterized by a powder X-ray diffractogram (XRPD) comprising reflections at 2-Theta angles of (6.0±0.2)°, (9.7±0.2)° and (12.0±0.2)°, when measured at 20° C. with Cu-Kalpha radiation having a wavelength of 0.15419 nm, in particular as disclosed in reference example A) herein.

46. The process of any one of embodiments 28 to 29 or 31 to 45, wherein the crystalline form obtained in (1) or (1-1) or (2) or (2-1) is characterized by having a XRPD comprising all reflections marked as bold in Table 1-first column, when measured at 20° C. with Cu-Kalpha radiation having a wavelength of 0.15419 nm, in particular as disclosed in reference example A) herein.

47. The process of any one of embodiments 28 or 30 to 44, wherein the crystalline form obtained in (1) or (1-2) or (2)

or (2-1) is characterized by a powder X-ray diffractogram (XRPD) comprising reflections at 2-Theta angles of (12.7±0.2)°, (20.7±0.2)°, (24.2±0.2)° and (25.4±0.2)°, when measured at 20° C. with Cu-Kalpha radiation having a wavelength of 0.15419 nm, in particular as disclosed in reference example A) herein.

48. The process of any one of embodiments 28 or 30 to 45 or 47, wherein the crystalline form obtained in (1) or (1-2) or (2) or (2-2) is characterized by having a XRPD comprising all reflections marked as bold in Table 1-second column, when measured at 20° C. with Cu-Kalpha radiation having a wavelength of 0.15419 nm, in particular as disclosed in reference example A) herein.

49. The process of any one of embodiments 28 to 48, wherein (1) or (1-2) is carried out by
   (1') dissolving N-{4-[(6,7-dimethoxy-4-quinolinyl)oxy]phenyl}-N'-(4-fluorophenyl)-1,1-cyclopropanedicarboxamide in a solvent selected from a $C_1$-$C_4$ alcohol, obtaining a mixture and treating said mixture with hydrochloric acid (HCl) or with phosphoric acid, preferably with hydrochloric acid (HCl) obtaining the crystalline form according to any one of embodiments 1 to 27, preferably according to anyone of embodiments 15 to 27.

50. The process of embodiment 49, wherein in (1') the $C_1$-$C_4$ alcohol is selected from methanol for the preparation of the crystalline form of any one of embodiments 1 to 14 and from ethanol for the preparation of the crystalline form of any one of embodiments 15 to 27.

51. The process of any one of embodiments 28 to 29 or 31 to 46, wherein prior to (1) or (1-2) the phosphate salt of (1) or (1-2) is prepared by a process comprising
   (A) dissolving or slurrying N-{4-[(6,7-dimethoxy-4-quinolinyl)oxy]phenyl}-N'-(4-fluorophenyl)-1,1-cyclopropanedicarboxamide in acetone and obtaining a mixture (A);
   (B) dissolving or slurrying phosphoric acid in tetrahydrofuran, obtaining a mixture (B);
   (C) combining the mixture (A) and the mixture (B), obtaining the N-{4-[(6,7-dimethoxy-4-quinolinyl)oxy]phenyl}-N'-(4-fluorophenyl)-1,1-cyclopropanedicarboxamide phosphate salt;
   (D) optionally subjecting the salt of (C) to temperature cycling;
   (E) isolating the N-{4-[(6,7-dimethoxy-4-quinolinyl)oxy]phenyl}-N'-(4-fluorophenyl)-1,1-cyclopropanedicarboxamide phosphate salt from its mother liquor.

52. The process of embodiment 51, wherein the temperature cycling of (D) is carried out at a temperature in the range of from 20 to 45° C.

53. The process of embodiment 51 or 52, wherein the temperature cycling of (D) is carried out in cycles wherein each cycle is preferably carried out for a period in the range of 2 to 5 h, preferably of from 3 to 4 h.

54. The process of any one of embodiments 51 to 53, wherein the temperature cycling of (D) is preferably carried out for an overall time of 2 to 4 days, preferably 3 days.

55. The process of any one of embodiments 52 to 54, wherein the temperature cycling is carried out with hold periods, wherein the cooling rate between hold periods is preferably of 1° C./min.

57. A crystalline form of N-{4-[(6,7-dimethoxy-4-quinolinyl)oxy]phenyl}-N'-(4-fluorophenyl)-1,1-cyclopropanedicarboxamide phosphate salt obtainable or obtained according to the process of any one of the embodiments 28 to 29, 31 to 47, 52 to 55

58. A crystalline form of N-{4-[(6,7-dimethoxy-4-quinolinyl)oxy]phenyl}-N'-(4-fluorophenyl)-1,1-cyclopropanedicarboxamide hydrochloride salt obtainable or obtained according to the process of any one of the embodiments 28, 30 to 45, 48 to 51.

59. A pharmaceutical composition comprising an effective amount of the crystalline form of any one of embodiments 1 to 27 and at least one pharmaceutically acceptable excipient.

60. The pharmaceutical composition of embodiment 59, wherein the crystalline form is according to any one of embodiments 1 to 14.

61. The pharmaceutical composition of embodiment 59, wherein the crystalline form is according to any one of embodiments 15 to 27.

62. The pharmaceutical composition of any one of embodiments 59 to 61, wherein the at least one pharmaceutically acceptable excipient is selected from a filler, a disintegrant, a glidant and a lubricant.

63. The pharmaceutical composition of any one of embodiments 59 to 62, which is a pharmaceutical composition for oral administration.

64. The pharmaceutical composition of embodiment 63, wherein the pharmaceutical composition for oral administration is a tablet or a capsule, preferably the capsule is a hard gelatin capsule.

65. The pharmaceutical composition of any one of embodiments 60 to 64, wherein the effective amount of the crystalline form is in the range of 20 to 80 mg.

66. Use of the crystalline form of any one of embodiments 1 to 27, preferably of any one of embodiments 1 to 13 for the preparation of a pharmaceutical composition.

67. The crystalline form of any one of embodiments 1 to 27 or the pharmaceutical composition of any one of embodiments 59 to 65 for use as a medicament.

68. The crystalline form for use of embodiment 66, which is the crystalline form according to anyone of embodiments 1 to 14.

69. The crystalline form for use of embodiment 68, which is the crystalline form according to anyone of embodiments 15 to 27.

70. The crystalline form of any one of embodiments 1 to 27 or 57 and 58 or the pharmaceutical composition of any one of embodiments 59 to 65 for use as a medicament in the treatment or prevention of cancer, preferably a thyroid cancer, more preferably metastatic medullary thyroid cancer.

71. The crystalline form for use of embodiment 70, which is the crystalline form according to anyone of embodiments 1 to 14.

72. The crystalline form for use of embodiment 70, which is the crystalline form according to anyone of embodiments 15 to 27.

74. A method of treating or preventing cancer, preferably a thyroid cancer, more preferably metastatic medullary thyroid cancer comprising administering the crystalline form of any one of embodiments 1 to 27 or the pharmaceutical composition of any one of embodiments 59 to 65 to a patient.

75. A composition comprising cabozantinib phosphate Form A, wherein the composition comprises at least 90 weight-% of cabozantinib phosphate Form A, more preferably at least 95 weight-% of cabozantinib phosphate Form A, even more preferably at least 97 weight-% of cabozantinib phosphate Form A, most preferably at least 99 weight-% of cabozantinib phosphate Form A, based on the weight of cabozantinib phosphate in the composition.

76. A composition comprising cabozantinib hydrochloride Form A-1, wherein the composition comprises at least 90 weight-% of cabozantinib hydrochloride Form A-1, more preferably at least 95 weight-% of cabozantinib hydrochloride Form A-1, even more preferably at least 97 weight-% of cabozantinib hydrochloride Form A-1, most preferably at least 99 weight-% of cabozantinib hydrochloride Form A-1, based on the weight of cabozantinib hydrochloride in the composition.

77. A process for the preparation of the crystalline form according to any one of embodiments 1 to 27, preferably according to any one of embodiments 1 to 14 comprising:
   (1) crystallizing N-{4-[(6,7-dimethoxy-4-quinolinyl)oxy]phenyl}-N'-(4-fluorophenyl)-1,1-cyclopropanedicarboxamide phosphate or N-{4-[(6,7-dimethoxy-4-quinolinyl)oxy]phenyl}-N'-(4-fluorophenyl)-1,1-cyclopropanedicarboxamide hydrochloride in a solvent consisting of an a $C_1$-$C_4$ alcohol, obtaining the crystalline form according to any one of embodiments 1 to 27, preferably according to any one of embodiments 1 to 14, wherein the crystallizing is carried out at a temperature in the range of from 10° C. to 50° C.;
   (2) optionally drying the crystalline form obtained from (1), obtaining the crystalline form according to any one of embodiments 1 to 27, preferably according to any one of embodiments 1 to 14.

78. A process for the preparation of a crystalline form of N-{4-[(6,7-dimethoxy-4-quinolinyl)oxy]phenyl}-N'-(4-fluorophenyl)-1,1-cyclopropanedicarboxamide phosphate according to any one of embodiments 1 to 14 comprising
   (1-1) crystallizing N-{4-[(6,7-dimethoxy-4-quinolinyl)oxy]phenyl}-N'-(4-fluorophenyl)-1,1-cyclopropanedicarboxamide phosphate in a solvent consisting of a $C_1$-$C_4$ alcohol, obtaining the crystalline form of any one of embodiments 1 to 14, wherein the crystallizing is carried out at a temperature in the range of from 10° C. to 50° C.;
   (2-1) optionally drying the crystalline form obtained from (1-1) obtaining the crystalline form of any one of embodiments 1 to 14.

79. A process for the preparation of a crystalline form of N-{4-[(6,7-dimethoxy-4-quinolinyl)oxy]phenyl}-N'-(4-fluorophenyl)-1,1-cyclopropanedicarboxamide hydrochloride according to any one of embodiments 15 to 27, comprising
   (1-2) crystallizing N-{4-[(6,7-dimethoxy-4-quinolinyl)oxy]phenyl}-N'-(4-fluorophenyl)-1,1-cyclopropanedicarboxamide hydrochloride in a solvent consisting of a $C_1$-$C_4$ alcohol, obtaining the crystalline form of any one of embodiments 15 to 27, wherein the crystallizing is carried out at a temperature in the range of from 10° C. to 50° C.;
   (2-2) optionally drying the crystalline form obtained from (1-2) of any one of embodiments 15 to 27.

The present invention is further illustrated by the following examples.

EXAMPLES

Reference Examples: Determination of Physical Parameters
A) X-Ray Powder Diffraction Pattern (XRPD)

XRPD analysis was carried out on a Siemens D5000 diffractometer, scanning the samples between 3 and 50 or 30° 2-theta. For samples of less than 100 mg, 10-20 mg of material was gently compressed onto a glass disc inserted into an XRPD sample holder. For samples of more than 100 mg, ca. 100 mg of material was gently compressed into a plastic XRPD sample holder to ensure a smooth sample surface, just above the level of the sample holder. The sample was then loaded into the diffractometer running in reflection mode and analyzed using the following experimental conditions.

| Raw Data Origin | Siemens-binary |
| --- | --- |
| V2 (.RAW) Start Position [°2Th.] | 3.0000 |
| End Position [°2Th.] | 30.000 or 50.000 |
| Step Size [°2Th.] | 0.0200 |
| Scan Step Time [s] | 1 |
| Scan Type | Continuous |
| Offset [°2Th.] | 0.0000 |
| Divergence Slit Type | Fixed |
| Divergence Slit Size [°] | 2.0000 |
| Specimen Length [mm] | various |
| Receiving Slit Size [mm] | 0.2000 |
| Measurement Temperature [° C.] | 20.00 |
| Anode Material | Cu |
| K-Alpha1, 2 | 0.15419 |
| K-Beta [Å] | 1.39225 |
| K-A2/K-A1 Ratio | 0.50000 |
| (nominal) Generator Settings | 40 mA, 40 kV |
| Diffractometer Type | d5000 |
| Goniometer Radius [mm] | 217.50 |
| Incident Beam Monochromator | No |
| Diffracted Beam Monochromator | Graphite |
| Spinning | No |

B) Organic Solvent Content: Thermogravimetric Analysis (TGA)

Approximately, 5-10 mg of material was accurately weighed into an open aluminum pan and loaded into a simultaneous thermogravimetric/differential thermal analyzer (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 cm³/min.

C) Water Content: Dynamic Vapour Sorption (DVS)

Approximately 10-20 mg of sample was placed into a vapour sorption balance pan and loaded into a DVS-1 dynamic vapour sorption balance by Surface Measurement Systems. The sample was subjected to a ramping profile from 20-90% relative humidity (RH) at 10% increments, maintaining the sample at each step until a stable weight had been achieved (99.5% step completion). After completion of the sorption cycle, the sample was dried using the same procedure, but all the way down to 0% RH and finally taken back to the starting point of 20% RH. The weight change during the sorption/desorption cycles were plotted, allowing for the hygroscopic nature of the sample to be determined.

D) Polarised Light Microscopy (PLM)

The presence of birefringence was determined using an Olympus BX50 polarizing microscope, equipped with a Motic camera and image capture software (Motic Images Plus 2.0). All images were recorded using the 20× objective lens, unless otherwise stated.

E) High Performance Liquid Chromatography-Ultraviolet Detection (HPLC-UV)

HPLC analysis was performed according to the following conditions:

Instrument: Agilent 1100

Column: Grace Smart RP 185 t 150×4.6 mm

Column Temperature: 30° C. UV wavelength: 249 nm
  Injection Volume: 10 µl

Flow Rate: 1.2 ml/min
Mobile Phase A: 0.1% Phosphoric acid
Mobile Phase B: 0.1% Phosphoric acid in acetonitrile
Gradient program:

| Time (minutes) | Solvent B [%] |
|---|---|
| 0 | 5 |
| 30 | 90 |
| 30.1 | 5 |
| 40 | 5 |

F) Water Content: Karl Fischer Coulometric Titration (KF)

Ca. 10-20 mg of solid material was accurately weighed into a container and the weight noted. The solid was then manually introduced into the titration cell of a Mettler Toledo C30 Compact Titrator. The titration was initiated once the sample had fully dissolved in the cell. The vial was back-weighed after the addition of the solid and the weight of the added solid entered into the instrument. The water content was calculated automatically by the instrument as a percentage and the data printed.

G) Aqueous Solubility Measurements

Each salt was individually slurried in deionized water and subjected to shaking for ca. 24 h at ambient temperature (ca. 22° C.). The resulting saturated solutions were filtered and analyzed by HPLC analysis. XRPD analysis was carried out on any solid retained after the solubility experiment.

H) Stoichiometry Determination: Ion Chromatography

The following conditions were used:
Sample Preparation: 0.05 mg/mL for phosphate
 0.06 mg/mL for hydrochloride
Instrument: Dionex ED 40 Electrochemical Detector, GP50 Gradient Pump, AS 1000 Autosampler, ASRS Ultra 11 4 mm suppressor
Column: Ion Pac AS14A-5 µm, 150 mm×3 mm
Guard Column: Ion Pac AGS14A-5 µm, 30 mm×3 mm
Column Temperature: 30° C.
Detection: Suppressed conductivity (suppressor current 50 mA)
Injection Volume: 25 µl (variable)
Flow Rate: 0.8 ml/min
Mobile Phase: 8 mM $Na_2CO_3$/1 mM $NaHCO_3$
Run time: 15 minutes Example 1

Preparation of Cabozantinib Phosphate Form A 0.5 g of cabozantinib free base was dissolved in 0.5 mL acetone. Approximately 1 equivalent of phosphoric acid was dissolved in 0.4 mL tetrahydrofuran. The cabozantinib free base solution was added to the phosphoric acid solution. Whilst stirring, the resulting slurry was temperature cycled between 22 and 40° C. in 4 hour cycles for 72 h.

The resulting solid was suspended in 10 mL of methanol and the slurry was subjected to temperature cycling between 22° C. and 40° C. in 4 hour cycles for ca. 3 days. The cooling/heating rate between hold periods is approximately 1° C./minute.

The XRPD diffractogram of the phosphate salt indicated the material to be crystalline. The XRPD diffractogram after recrystallization with methanol was different from the XRPD of the solid obtained from acetone/THF. The new crystalline form obtained shows a high level of crystallinity. The XRPD diffractogram is shown in FIG. 1.

The ion chromatography indicated a stoichiometry of about 1:0.9 cabozantinib:phosphate.

The water content was found to be 0.5 weight-% by KF analysis.

The TG/DTA analysis showed a ca. 0.3 weight-% weight loss at a temperature below ca. 210° C. indicating an anhydrous salt form in nature. The TG/DTA curve is shown in FIG. 3.

The crystalline form was found to take up water to about 1 weight-% between 20% and 70% RH when measured by DVS analysis (measured according to reference example C and as shown in FIG. 6).

The solubility of the crystal form in water was found to be of 0.09 mg/ml.

Example 2

Preparation of Cabozantinib Hydrochloride Form A-1

Ethanol (400 µL) was added to 500.9 mg of cabozantinib free base. One equivalent of HCl in 400 µL of ethanol was added to the vial containing the freebase. The resultant experiment was stirred at room temperature for ca. 4 hrs. The sample was then placed under vacuum at room temperature for solvent evaporation overnight. To the resulting dried material, ca. 2 mL ethanol were added and the sample was stirred at room temperature for ca. 7 hours. The sample was then temperature cycled between 22° C. and 40° C. in 4 hour cycles for ca. 3 days whilst shaking. The cooling/heating rate between hold periods was approximately 1° C./minute. After temperature cycling, the sample was isolated and placed into a dessicator and dried at room temperature for ca. 1 day.

Figure 2:
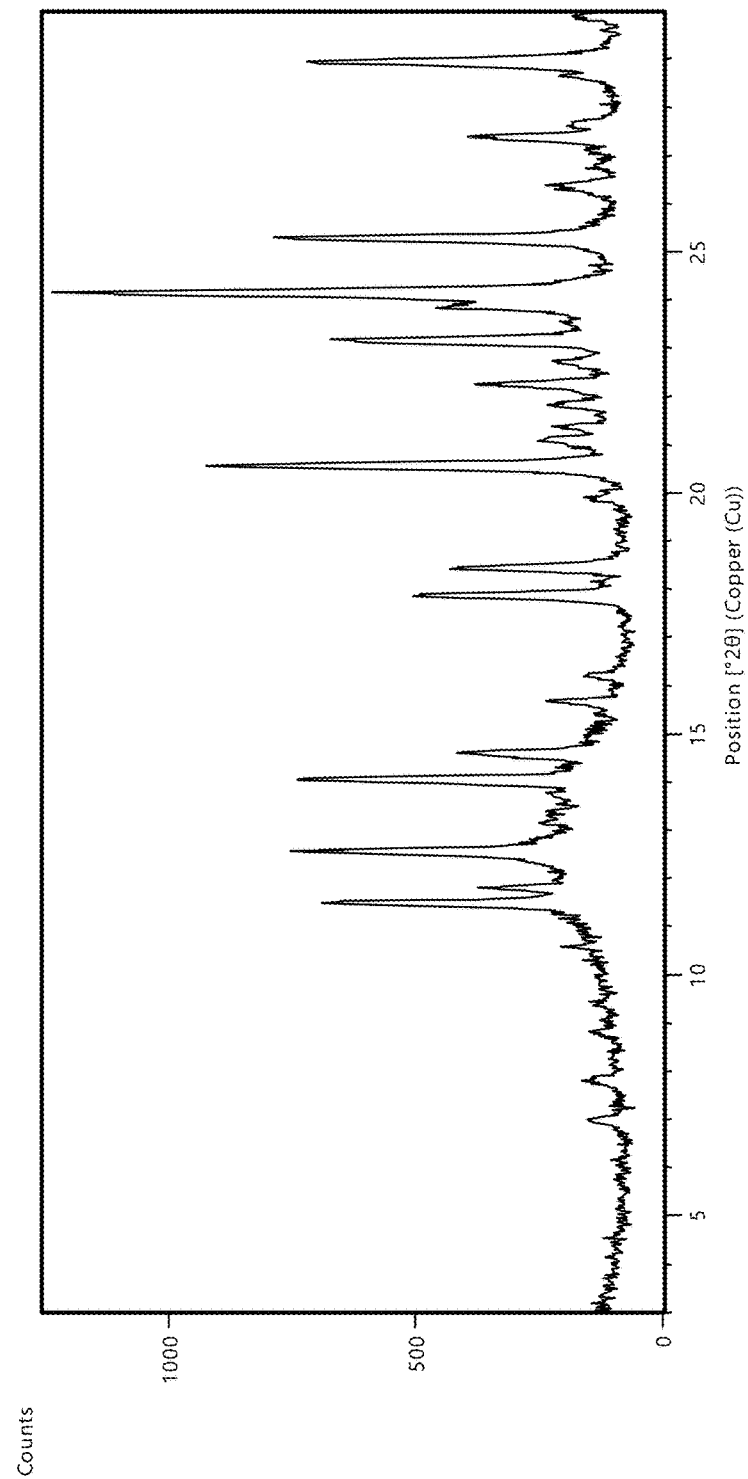
FIG. 2: Representative XRPD of the crystalline Form A-1 of cabozantinib hydrochloride.

The XRPD diffractograms of the wet and of the dried form were recorded. The XRPD diffractograms indicated the material to be crystalline. The XRPD diffractogram is shown in FIG. 2

Ion chromatography indicated a stoichiometry of about 1:0.8 cabozantinib:chloride.

The water content was found to be 0.2 weight % by KF analysis.

The TG/DTA analysis showed a ca. 0.5 weight-% loss at a temperature below ca. 215° C. indicating an anhydrous salt form. The TG/DTA curve is shown in FIG. 4.

The crystalline form was found to be non hygroscopic with a water up-take of ca. 0.07% between 20% and 70% RH measured by DVS analysis as measured according to reference example C and as shown in FIG. 7.

The solubility of the crystal form in water was found to be 0.21 mg/ml.

The examples 3 and 4 below are specific and preferred examples for capsules and tablets prepared from a crystalline form of the present invention. One skilled in the art will appreciate that changes and modifications to the described examples can be practices within the scope of the appended claims.

Example 3

Capsule Composition Comprising Crystalline Cabozantinib Phosphate Form A

Drug substance and excipients are screened and blended using typical manufacturing equipment. Pharmaceutical capsule compositions such as exemplified below are then prepared from the blend.

A pharmaceutical capsule composition comprising 20 mg cabozantinib in form of its non-hygroscopic phosphate salt Form A according Table 3.

TABLE 3

| Ingredient | mg/unit dose |
| --- | --- |
| Cabozantinib phosphate Form A | 24 |
| Silicified microcrystalline Cellulose | 197.75 |
| Croscarmellose sodium | 12.5 |
| Sodium starch glycolate | 12.5 |
| Fumed Silica | 0.75 |
| Stearic acid | 2.5 |
| Total Fill Weight | 250 |

A pharmaceutical capsule composition comprising 80 mg cabozantinib in form of its non-hygroscopic phosphate salt Form A according Table 4.

TABLE 4

| Ingredient | mg/unit dose |
| --- | --- |
| Cabozantinib phosphate Form A | 95.6 |
| Silicified microcrystalline Cellulose | 152.73 |
| Croscarmellose sodium | 14.5 |
| Sodium starch glycolate | 14.5 |
| Fumed Silica | 0.87 |
| Stearic acid | 5.8 |
| Total Fill Weight | 284 |

A pharmaceutical capsule composition comprising 100 mg cabozantinib in form of its non-hygroscopic phosphate salt Form A according Table 5.

TABLE 5

| Ingredient | mg/unit dose |
| --- | --- |
| Cabozantinib phosphate Form A | 95.6 |
| Silicified microcrystalline Cellulose | 75.8 |
| Croscarmellose sodium | 10.0 |
| Sodium starch glycolate | 10.0 |
| Fumed Silica | 0.6 |
| Stearic acid | 4.0 |
| Total Fill Weight | 196 |

Example 4

Tablet Compositions Comprising Crystalline Cabozantinib Phosphate Form A

Drug substance and excipients are screened and blended using typical manufacturing equipment. Tablets such as exemplified below are then prepared from the blend.

A tablet comprising 20, 40, 60, or 80 mg cabozantinib in form of its non-hygroscopic phosphate salt Form A according to table 6.

TABLE 6

| Ingredient | % w/w |
| --- | --- |
| Cabozantinib phosphate Form A | 30.0 |
| Microcrystalline Cellulose | q.s. |
| Hydroxypropyl Cellulose | 3 |
| Poloxamer | 0-3 |
| Croscarmellose Sodium | 6.2 |

TABLE 6-continued

| Ingredient | % w/w |
| --- | --- |
| Colloidal Silicon Dioxide | 0.5 |
| Magnesium Stearate | 0.75 |
| Total | 100.00 |

A tablet comprising 20, 40, 60, or 80 mg cabozantinib in form of its non-hygroscopic phosphate salt Form A according to table 7.

TABLE 7

| Ingredient | Function | % w/w |
| --- | --- | --- |
| Cabozantinib phosphate Form A | Active Ingredient | 30.0 |
| Microcrystalline Cellulose (Avicel PH-102) | Filler | 40.0 |
| Lactose Anhydrous (60 M) | Filler | 19.95 |
| Hydroxypropyl Cellulose (EXF) | Binder | 3.0 |
| Croscarmellose Sodium (Ac-Di-Sol) | Disintegrant | 6.0 |
| Colloidal Silicon Dioxide, | Glidant | 0.3 |
| Magnesium Stearate | Lubricant | 0.75 |
| Opadry Yellow Film Coating which includes: | | |
| HPMC 2910/Hypromellose 6 cp Titanium dioxide Triacetin Iron Oxide Yellow | Film Coating | 4.00 |

The invention claimed is:

1. A crystalline form of N-{4-[(6,7-dimethoxy-4-quinolinyl)oxy]pheny}-N'-(4-fluorophenyl)-1,1-cyclopropanedicarboxamide (cabozantinib) phosphate characterized by a powder X-ray diffractogram (XRPD) comprising reflections at 2-Theta angles of (6.0±0.2)°, (9.7±0.2)° and (12.0±0.2)°, when measured at 20° C. with Cu-Kalpha radiation having a wavelength of 0.15419 nm.

2. The crystalline form of claim 1 characterized by the XRPD comprising reflections at 2-Theta angles of (6.0±0.2)°, (9.7±0.2)°, (12.0±0.2)° and (19.4±0.2)°, when measured at 20° C. with Cu-Kalpha radiation having a wavelength of 0.15419 nm.

3. The crystalline form of claim 1, characterized by having a TG/DTA curve showing a weight loss of at most 1.0 weight-% based on the weight of the crystalline form.

4. The crystalline form of claim 1 characterized by having a water content of at most 1.0 weight-%, based on the weight of the crystalline form, as determined by Karl Fischer coulometric titration (KF).

5. A crystalline form of N-{4-[(6,7-dimethoxy-4-quinolinyl)oxy]pheny}-N'-(4-fluorophenyl)-1,1-cyclopropanedicarboxamide hydrochloride salt characterized by a XRPD comprising reflections at 2-Theta angles of (12.7±0.2)°, (20.7±0.2)°, (4.2±0.2)° and (25.4±0.2)°, when measured at 20° C. with Cu-Kalpha radiation having a wavelength of 0.15419 nm.

6. The crystalline form of claim 5, characterized by a XRPD comprising reflections at 2-Theta angles of (12.7±0.2)°, (18.0±0.2)°, (20.7±0.2)°, (24.2±0.2)°, (25.4±0.2)°, when measured at 20 ° C. with Cu-Kalpha radiation having a wavelength of 0.15419 nm.

7. The crystalline form of claim 5, characterized by having a TG/DTA curve showing a weight loss equal or less than 1 weight-% based on the weight of the crystalline form.

8. The crystalline form of claim 5, characterized by having a water content of at most 1.0% based on the weight of the crystalline form as determined by Karl Fischer coulometric titration (KF).

9. A process for the preparation of a crystalline form of a salt of cabozantinib comprising:
   (1) crystallizing N-{4-[(6,7-dimethoxy-4-quinolinyl)oxy]pheny}-N'-(4-fluorophenyl)-1,1-cyclopropanedicarboxamide phosphate salt or the N-{4-[(6,7-dimethoxy-4-quinolinyl)oxy]phenyl}-N'-(4-fluorophenyl)-1,1-cyclopropanedicarboxamide hydrochloride salt in a solvent consisting of a C1-C4 alcohol, wherein the crystallizing is carried out at a temperature of from 10° C. to 50° C., obtaining a crystalline form; and
   (2) optionally drying the crystalline form of (1); and
   wherein the crystalline form of the phosphate salt is characterized by a powder X-ray diffractogram (XRPD) comprising reflections at 2-Theta angles of (6.0±0.2)°, (9.7±0.2)° and (12.0±0.2)°, when measured at 20 ° C. with Cu-Kalpha radiation having a wavelength of 0.15419 nm, and
   wherein the crystalline form of the hydrochloride salt is characterized by a XRPD comprising reflections at 2-Theta angles of (12.7±0.2)°, (20.7±0.2)°, (24.2±0.2)° and (25.4±0.2)°, when measured at 20° C. with Cu-Kalpha radiation having a wavelength of 0.15419nm.

10. The process of claim 9, wherein the alcohol is selected from methanol and the crystalline form is the crystalline form of the phosphate salt.

11. The process of claim 9, wherein the alcohol is selected from ethanol and the crystalline form is the crystalline form of the hydrochloride salt, further comprising the step
   (2) drying the crystalline form obtained from step (1) at room temperature.

12. A pharmaceutical composition comprising an effective amount of the crystalline form of claim 1 and at least one pharmaceutically acceptable excipient.

13. A method of treating thyroid cancer, comprising administering the crystalline form of claim 1 to a patient.

* * * * *